(12) United States Patent
Abe

(10) Patent No.: US 8,496,590 B2
(45) Date of Patent: Jul. 30, 2013

(54) ULTRASONIC DIAGNOSTIC EQUIPMENT AND ULTRASONIC IMAGE PROCESSING APPARATUS

(75) Inventor: Yasuhiko Abe, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 213 days.

(21) Appl. No.: 12/892,167

(22) Filed: Sep. 28, 2010

(65) Prior Publication Data

US 2011/0077516 A1 Mar. 31, 2011

(30) Foreign Application Priority Data

Sep. 30, 2009 (JP) ................................ 2009-228577

(51) Int. Cl.
*A61B 8/00* (2006.01)

(52) U.S. Cl.
USPC .......................................... 600/443; 600/447

(58) Field of Classification Search
USPC ........................................................ 600/443
See application file for complete search history.

(56) References Cited

U.S. PATENT DOCUMENTS

| 6,120,453 | A | * | 9/2000 | Sharp | 600/463 |
| 2008/0304730 | A1 | * | 12/2008 | Abe | 382/131 |
| 2009/0054776 | A1 | * | 2/2009 | Sasaki | 600/443 |
| 2010/0268085 | A1 | * | 10/2010 | Kruecker et al. | 600/443 |

FOREIGN PATENT DOCUMENTS

| JP | 3878343 | 11/2006 |
| JP | 2009-72593 | 4/2009 |

OTHER PUBLICATIONS

Xiaoguang Lu, et al., "AutoMPR: Automatic Detection of Standard Planes in 3D Echocardiography," IEEE ISBI 2008, pp. 1279-1282.

* cited by examiner

*Primary Examiner* — Jonathan Cwern
(74) *Attorney, Agent, or Firm* — Olbon, Spivak, McClelland, Maier & Neustadt, L.L.P.

(57) ABSTRACT

According to one embodiment, an ultrasonic diagnostic equipment which executes ultrasound scanning over a two-dimensional or three-dimensional region in a subject, includes a cross-section detecting unit which detects an MPR position corresponding to at least one predetermined reference cross-section of the heart by use of at least one volume data obtained by executing ultrasound scanning over the three-dimensional region containing at least a portion of the heart of the subject, an image generating unit which generates an MPR image corresponding to the MPR position, a display unit which displays the MPR image, and an image acquisition unit which executes ultrasound scanning over the two-dimensional region in the subject under the reference of the MPR position to obtain at least one two-dimensional image regarding the two-dimensional region.

13 Claims, 5 Drawing Sheets

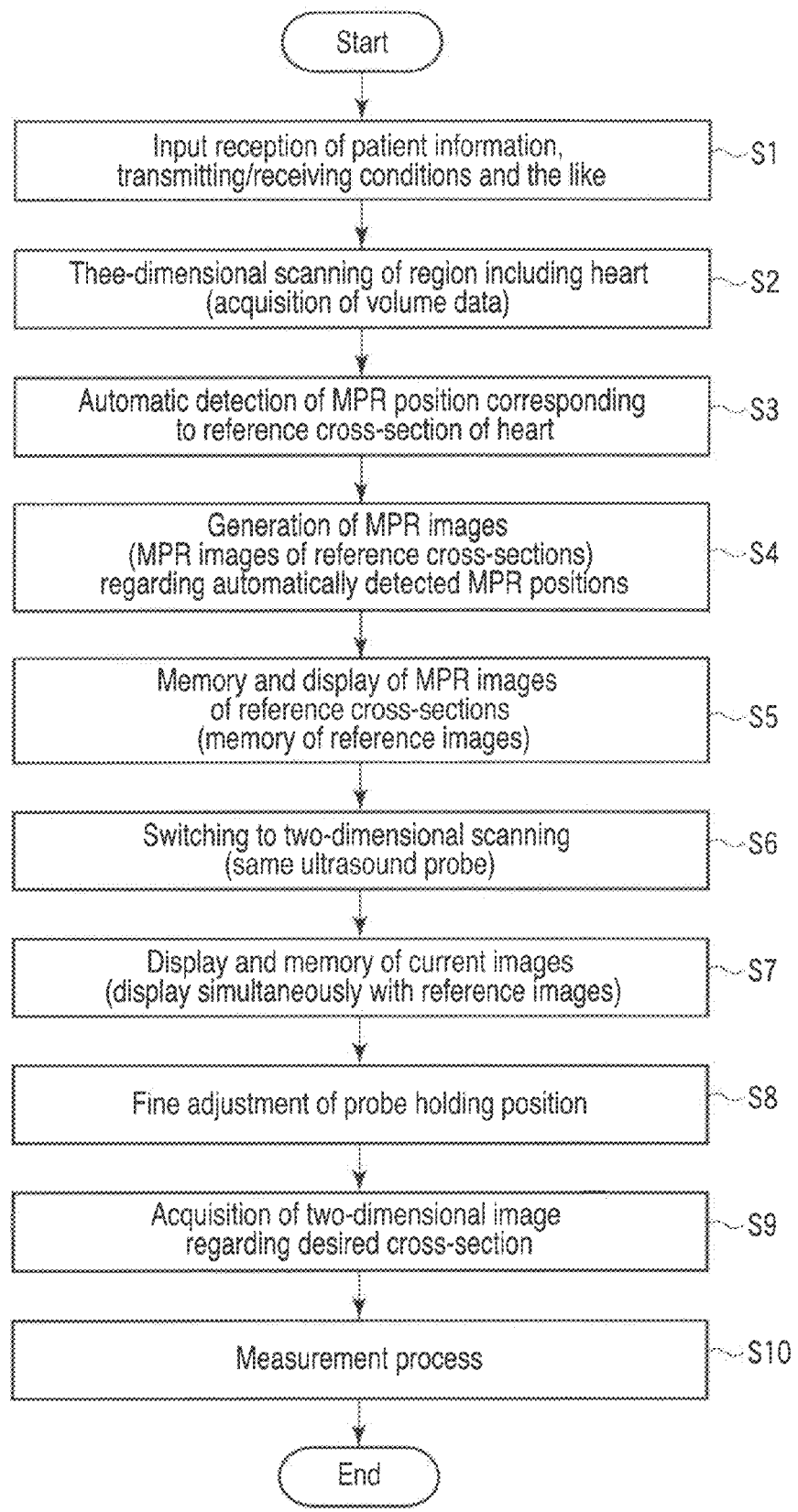
F I G. 2

ULTRASONIC DIAGNOSTIC EQUIPMENT AND ULTRASONIC IMAGE PROCESSING APPARATUS

CROSS-REFERENCE TO RELATED APPLICATIONS

This application is based upon and claims the benefit of priority from Japanese Patent Application No. 2009-228577, filed Sep. 30, 2009; the entire contents of which are incorporated herein by reference.

FIELD

Embodiments described herein relate generally to an ultrasonic diagnostic equipment and an ultrasonic image processing apparatus.

BACKGROUND

With regard to a biological tissue such as the cardiac muscle, the objective and quantitative estimation of its functions is very important for the diagnosis of the tissue. In a routine examination of the heart by an ultrasonic diagnostic equipment and an ultrasonic image processing apparatus, there have been performed a volume measurement by a modified-simpson method using two-dimensional images obtained by apical approach (A4C (apical 4 chamber image), A2C (apical 2 chamber image) and the like) by two-dimensional scanning, and a measurement of an inner diameter shortening ratio (% FS) and a wall thickness from two-dimensional images obtained by extracting short axis images (SAX).

Further, a recent three-dimensional ultrasonic diagnostic equipment enables real time collection and display of three-dimensional ultrasonic images by scanning ultrasound beams in a three-dimensional manner. In addition, it has also been realized that arbitrary cross-sectional (Multi-planar Reconstruction: MPR) images are produced from collected three-dimensional image data and displayed. Then, the utilization of the MPR images enables the same various measurements as in the above conventional case.

However, in a case where the conventional ultrasonic diagnostic equipment and ultrasonic image processing apparatus are used to perform various measurements of the heart, for example, there are the following problems.

Firstly, when a cross-section of a vicinity of the heart apex is depicted in an apical approach image by use of two-dimensional scanning, it seems as if the heart apex portion can be depicted, even if the real heart apex position is not included within the scanned cross-section. Therefore, it is difficult to grasp a correct position of the scanned cross-section, and hence the heart apex portion cannot be correctly caught up in many cases. In addition, it also difficult that any one obtains, with an excellent reproducibility, the same apical approach images which pass through a correct central long axis. As the result, a volume measured underestimating a long axis length is underestimated, and such a case often occurs. Moreover, when the recognitions of the position of the heart apex portion for the depicted image are different among examiners, the measured values of volumes, EF and others are varied.

On the other hand, in a case where the cross-section of the vicinity of the heart apex is depicted in an apical approach image by use of three-dimensional scanning, the MPR image of the heart central long axis including the heart apex portion can be comparatively easily obtained. In this case, however, a spatial resolution and a temporal resolution are inferior to the case of the two-dimensional scanning. In consequence, an endocardial position relatively blurs by the restriction of the spatial resolution, and hence the position of an inner cavity is recognized to be more inside than in an actual case, whereby the volume is underestimated. In addition, the restriction of the temporal resolution relatively increases the variation of phases at the time of measurement, which deteriorates the reproducibility of the measurement results.

An object is to provide an ultrasonic diagnostic equipment and an ultrasonic image processing apparatus in which even a person who is not an expert can easily depict a reference cross-section by a correct two-dimensional scan which is necessary for the examination of the heart, and accuracy and reproducibility of a diagnosis using the reference cross-section can be enhanced.

BRIEF DESCRIPTION OF THE DRAWINGS

FIG. 2 is a flowchart showing a flow of a heart examination support process according to the first embodiment in accordance with a series of scan sequence.

DETAILED DESCRIPTION

Figure 1:
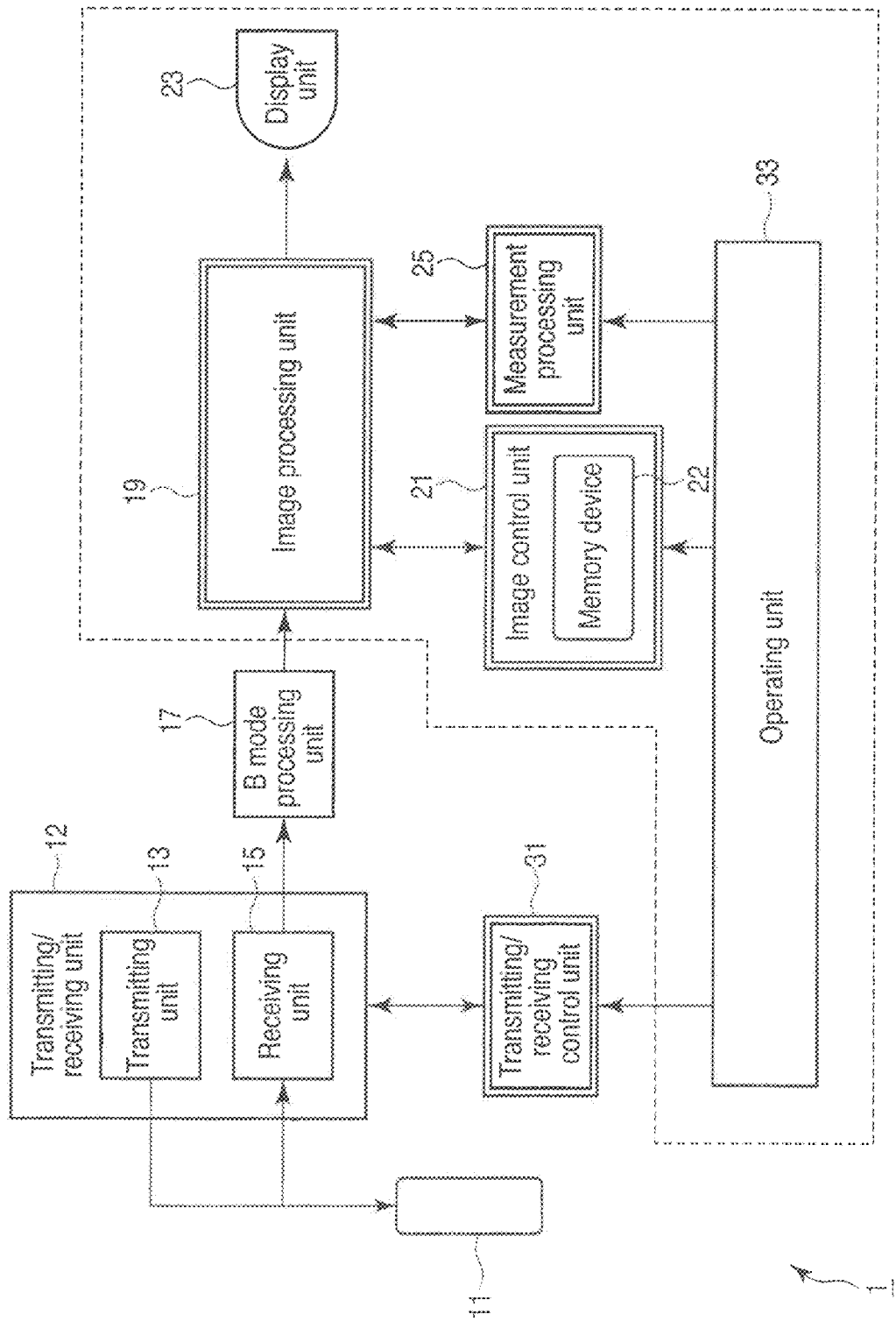
FIG. 1 is a constitutional view of an ultrasonic diagnostic equipment 1 according to a first embodiment.

Hereinafter, embodiments will be described with reference to the drawings. In the following description, constitutional elements having substantially the same function and configuration will be denoted by the same reference numerals, and overlapped explanations will be made only in cases where it is necessary.

In general, according to one embodiment an ultrasonic diagnostic equipment which executes ultrasound scanning over a two-dimensional or three-dimensional region in a subject, includes a cross-section detecting unit which detects an MPR position corresponding to at least one predetermined reference cross-section of the heart by use of at least one volume data obtained by executing ultrasound scanning over the three-dimensional region containing at least a portion of the heart of the subject, an image generating unit which generates an MPR image corresponding to the MPR position, a display unit which displays the MPR image, and an image acquisition unit which executes ultrasound scanning over the two-dimensional region in the subject under the reference of the MPR position to obtain at least one two-dimensional image regarding the two-dimensional region.

First Embodiment

FIG. 1 is a constitutional view of an ultrasonic diagnostic equipment 1 according to the present embodiment. This ultrasonic diagnostic equipment 1 comprises an ultrasound probe 11, a transmitting/receiving unit 12 having a transmitting unit 13 and a receiving unit 15, a B mode processing unit 17, an image processing unit 19, an image control unit 21 having a memory device 22, a display unit 23, a measurement processing unit 25, a transmitting/receiving control unit 31, and an operating unit 33. It is noted that if this embodiment is applied to an ultrasonic image processing apparatus, its constitutional elements are present within the broken line in FIG. 1.

The ultrasound probe 11 has a plurality of ultrasound vibrators which generate an ultrasound based on a drive signal from the transmitting unit 13 and convert a reflected wave from a subject to an electric signal, a matching layer provided on each ultrasound vibrator, a backing material which prevents the propagation of the ultrasound toward a back side from the ultrasound vibrators, and others. The ultrasound transmitted from the ultrasound vibrator 11 to the subject is backward scattered by a boundary of an acoustic impedance in inner tissues, fine scattering and others, and it is received by the ultrasound probe 11 as a reflected wave (echo).

It is noted that the ultrasound probe 11 in the present embodiment is a two-dimensional array probe where the ultrasound vibrators are arranged in a two-dimensional matrix state and which can scan a two-dimensional region and a three-dimensional region with the ultrasound.

The transmitting unit 13 has a delay circuit, a pulser circuit and others which are not shown. In the pulser circuit, a rate pulse for forming a transmitting ultrasound is repeatedly generated at a predetermined rate frequency fr Hz (cycle; 1/fr sec). Further, in the delay circuit, the ultrasound is converged in a beam state every channel, and a delay time necessary to determine a transmitting directivity is given to each rate pulse. The transmitting unit 13 applies a driving pulse every the vibrator at timing based on this rate pulse so that an ultrasound beam is formed toward a predetermined scan line.

The receiving unit 15 has an amplifier circuit, an A/D converter, an adder and others which are not shown. In the amplifier circuit, an echo signal caught through the probe 11 is amplified every channel. In the A/D converter, a delay time necessary to determine a receiving directivity to the amplified echo signal is given, and then in the adder, the processing of adding is performed. This adding gives rise to the generation of an ultrasound echo signal corresponding to a predetermined scan line.

The B mode processing unit 17 generates a B mode signal corresponding to amplitude strength of the ultrasound echo by subjecting the ultrasound echo signal received from the receiving unit 15 to an envelope detection process.

The image processing unit 19 generates a two-dimensional ultrasonic image or a three-dimensional ultrasonic image of the B mode by use of a two-dimensional distribution regarding a predetermined tomography of a B mode signal or a three-dimensional distribution regarding a predetermined region. Further, the image processing unit 19 executes the setting of an MPR position corresponding to a desired reference cross-section and the generation of the MPR image corresponding to the MPR position by use of volume data.

The image control unit 21 has a function as an information processing unit (a computer). Particularly, the image control unit 21 develops an exclusive program stored in the memory device 22 to execute a control and the like regarding a process of the heart examination support function (heart examination support process) which will be described later.

The display unit 23 displays an ultrasonic image, a predetermined operation screen and the like based on video signals from the image generation unit 21.

The measurement processing unit 25 executes measurement and estimation of a volume, an inner diameter shortening ratio and the like by use of an obtained ultrasonic image and volume data.

The operating unit 33 is connected to the device body and has a mouse or a track ball, a mode changeover switch, a key board and the like for executing various instructions from an operator, a setting instruction of a region of interest (ROI), a screen (image) freeze instruction, various image quality condition setting instructions, selection of the information of an arbitrary tissue motion and the like.

(Heart Examination Support Function)

Next, the heart examination support function of the ultrasonic diagnostic equipment 1 will be described. According to this function, in the heart examination by use of the ultrasonic diagnostic equipment, an automatic MPR position corresponding to the position of the reference cross-section of the heart is set to volume data obtained by the three-dimensional ultrasound scanning, and an ideal MPR image corresponding to the MPR position is displayed. Then, an ultrasound scanning region is automatically switched to a cross-section of a subject (the cross-section of the subject closest to the MPR position, or the cross-section of the subject at the substantially the same position as the MPR position) corresponding to a set ideal MPR position. By this function, the ultrasound scanning region is automatically switched from the three-dimensional region to the two-dimensional region in a state where the ideal MPR image is obtained by the three-dimensional ultrasound scanning (a state where a user keeps holding the position of the two-dimensional array probe). Therefore, the reference cross-section by the correct two-dimensional scanning which is necessary for the examination of the heart can easily be depicted even by a person who is not an expert, and the accuracy and reproducibility of a diagnosis using the reference cross-section can be enhanced.

It is noted that in the embodiment, as an example for concrete explanation, there is employed a motion information generation function in a case where an object of the diagnosis is the heart. However, the applicable object for the motion information generation function is not limited to the heart, and any region may be applied so long as it is a tissue where the reference cross-section exists in the ultrasound diagnosis. Examples of such a subject for the diagnosis include a carotid and an unborn baby.

FIG. 2 is a flowchart showing a flow of the heart examination support process regarding the first embodiment in accordance with a series of scan sequence. Hereinafter, the contents of the respective steps of the flowchart in FIG. 2 will be described.

[Input Reception of Patient Information, Transmitting/Receiving Conditions and the Like: Step S1]

Patient information and transmitting/receiving conditions (an image angle, a focus position, a transmitting/receiving voltage and the like) and others are input through the operating unit 33. The thus input information and conditions are automatically stored in the memory device 22 (Step S1).

[Three-Dimensional Scanning of Region Including Heart: Step S2]

Next, the transmitting/receiving control unit 31 executes a real time three-dimensional ultrasound scanning, with a region to be scanned being the three-dimensional region including the heart of the subject (Step S2). Specifically, for example, the volume data of time series (at least one heartbeat) regarding a desired observation portion of the heart of the subject is collected from an apical approach by use of a two-dimensional array probe, with a certain time being employed as a reference (an initial phase).

[Automatic Detection of MPR Position Corresponding to Reference Cross-Section of Heart: Step S3]

The image processing unit 19 automatically detects an MPR position corresponding to at least one reference cross-section of the heart with respect to at least one of the obtained volume data of the heart (Step S3). As an automatic detecting technique of this cross-section, there can be employed a technique (hereinafter referred to as "Auto-MPR") disclosed in, for example, Jpn. Pat. Appln. KOKAI Publication No. 2009-72593 and Non-patent Document 3. Further, examples of the reference cross-section of the heart include long axis images (A4C, A2C and A3C) having different rotation angles with respect to the central axis and short axis images (SAXA, SAXM and SAXB) having different levels in accordance with desired standards. In this step, the MPR positions on the volume data corresponding to these reference cross-sections are simultaneously detected by the Auto-MPR.

In this step, it is suitable to select an A4C cross-section and an A2C cross-section by the heart apex portion approach, as the reference cross-sections. The volume data obtained by the three-dimensional scanning with the proper heart apex approach contains a heart apex position. Accordingly, the user can extract, with an excellent reproducibility, the A4C image or the A2C image by the MPR which passes through the heart apex position under the recognition that "the image surely contains the heart apex position" by confirming the MPR position corresponding to the reference cross-section detected by the Auto-MPR, while finely adjusting the holding position and the direction of the ultrasound probe 11.

[Generation, Display, and Memory of MPR Images Regarding Detected MPR Positions: Steps S4 and S5]

Figure 3:
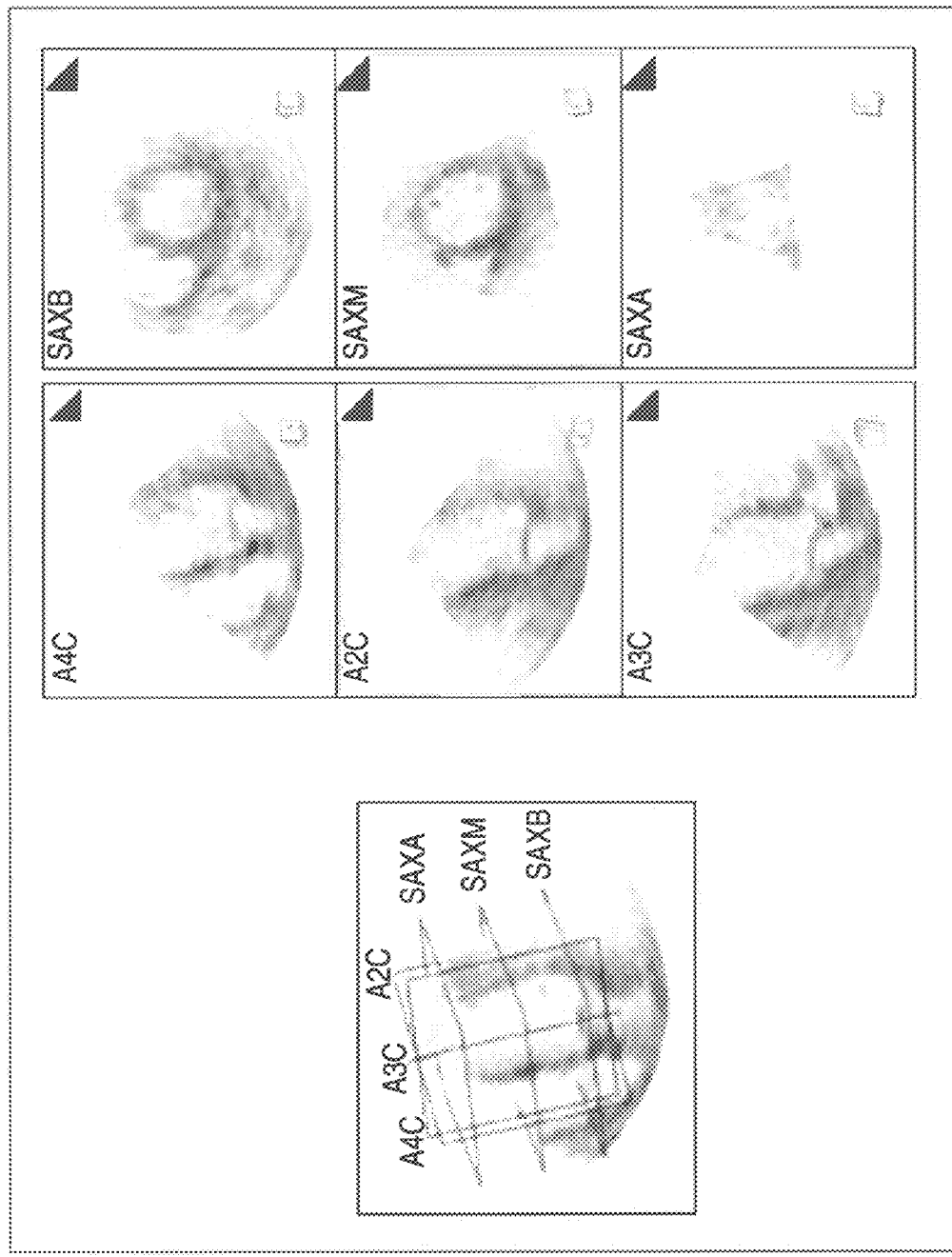
FIG. 3 is a view showing one example of a display mode of each MPR image corresponding to an automatically detected reference cross-section.

The image processing unit 19 generates an MPR image regarding the MPR position automatically detected on each volume data (Step S4). Here, two images of an A4C image and an A2C image are generated as long axis images, and three images of an SAXA image, an SAXM image and an SAXB image are generated as short axis images having different levels. The generated MPR images are automatically and sequentially displayed on the display unit 23 as reference images, for example, in forms shown in FIG. 3. Further, the displayed MPR images are automatically and sequentially stored in the memory device 22 (Step S5).

[Switching to Two-Dimensional Scanning, and Acquisition of Two-Dimensional Images: Steps S6 and S7]

The transmitting/receiving unit 31 automatically switches the region to be scanned to a cross-section of the subject (the cross-section of the subject closest to the MPR position, or the cross-section of the subject at the substantially the same position as the MPR position) corresponding to any one of MPR positions automatically detected from the three-dimensional region containing the heart, for example, in response to a predetermined operation (e.g., a dimensional switching operation of scanning) from the operating unit 33 (Step S6). After the switching, a two-dimensional image (a current image) regarding the cross-section of the subject corresponding to the MPR position is sequentially obtained and displayed on the display unit 23 at a real time (Step S7).

Figure 4:
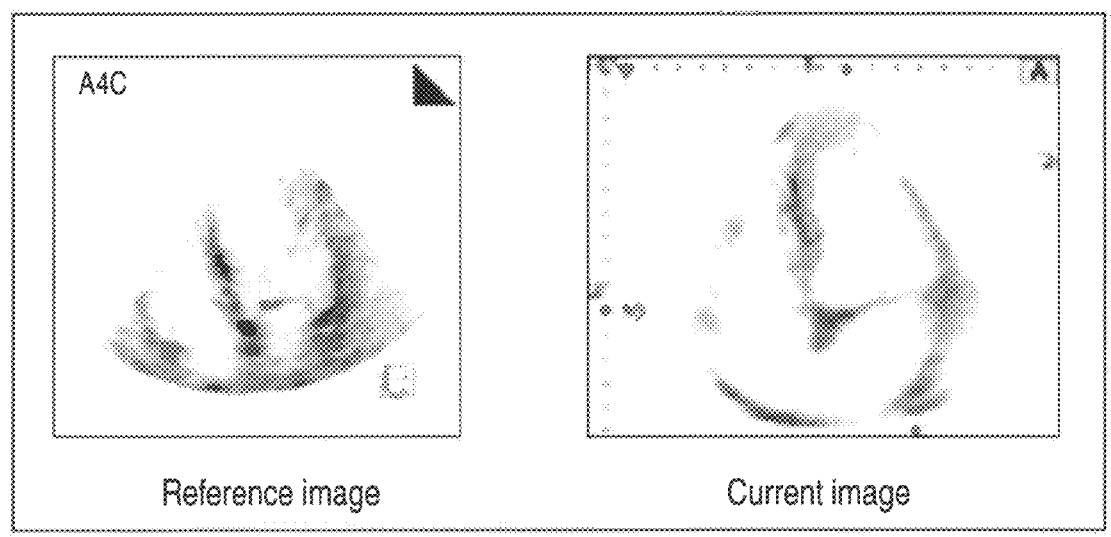
FIG. 4 is a view showing one example of a case where a two-dimensional image (current image) corresponding to the reference cross-section and an MPR image (reference image) corresponding to the reference cross-section are simultaneously displayed.

It is noted that the current image is displayed together with a reference image (i.e., an MPR image such as an A4C image or an A2C image) referred to in determining the cross-section of the subject corresponding to the current image. In this case, the current image and the reference image are preferably displayed, for example, side by side as shown in FIG. 4.

Further, it is considered to be ideal that each MPR image displayed as the above reference image corresponds to an image obtained when the ultrasound scanning is switched from the three-dimension to the two-dimension. Therefore, it is suitable that the MPR image at the three-dimensional scanning is stored in a retrospective manner, and the MPR image obtained when the ultrasound scanning is switched from the three-dimension to the two-dimension is read and displayed.

The MPR image as this reference image may be a still image in a predetermined cardiac phase at end-diastole or end-systole or a moving image of at least one heartbeat may be displayed.

Furthermore, as the combination of the reference image and the current image, for example, one example is to display only one cross-section of an image (the A4C image or the like) corresponding to the same cross-section. However, the combination of the reference image and the current image is not limited to the above example. For example, in the two-dimensional array probe, a plurality of cross-sections can be substantially simultaneously scanned, and hence there is also an example where images (e.g., the A4C image and the A2C image) corresponding to two kinds of cross-sections or images (e.g., the A4C image, the A2C image and the A3C image) corresponding to three kinds of cross-sections are simultaneously displayed. In addition, the reference image may be a configuration of a plurality of images corresponding to kinds of cross-sections containing the same cross-section as that of the current image, or the current image may be a configuration of a plurality of images corresponding to kinds of cross-sections containing the same cross-section as that of one reference image.

[Fine Adjustment of Probe Holding Position, and Acquisition of Two-Dimensional Image Regarding Desired Cross-Section: Steps S8 and S9]

The user finely adjusts the holding position of the ultrasound probe 11 while observing the current image and the reference image displayed on the display unit 23 (Step S8) and executes a predetermined operation (e.g., a freeze operation) at the time of acquisition of the two-dimensional image regarding a desired cross-section, whereby the two-dimensional image is freeze-displayed on the display unit 23 and simultaneously stored in the memory device 22 (Step S9).

It is noted that after the collection of the two-dimensional images necessary for measurement, the reference image, needless to say, may not be displayed by an automatic operation or a manual operation if necessary.

[Measurement Process: Step S10]

The measurement processing unit 25 executes a predetermined measurement process (e.g., a volume measurement process by a modified-simpson method) by use of the two-dimensional image regarding the correct reference cross-section obtained in Step S9 (Step S10). It is noted that the final measurement in the present embodiment is preferably performed on a diagnostic apparatus. However, the above example is not limited. For example, the two-dimensional image data collected by the diagnostic apparatus may be transferred to an analysis viewer such as an image processing workstation or the like through a network or the like to perform the measurement process in this analysis viewer.

Modified Example

In the above description, it has been explained that when the display of the MPR image of the plurality of reference cross-sections based on the three-dimensional scanning is switched to the display of the two-dimensional image (the current image) by ultrasound-scanning the two-dimensional region corresponding to any one of the reference cross-sections, the MPR image of the reference cross-sections is displayed simultaneously with the reference image. However, the present example is not limited. For example, after the ultrasound-scanned region is switched from the three-dimensional region to the two-dimensional region, the two-dimensional image (current image) may only be displayed, without displaying the reference image. Even in such a configuration, the ultrasound-scanned region can be switched from the three-dimensional region to the two-dimensional region while the user holds the position of the two-dimensional array probe in a state where the MPR image of the ideal reference cross-section is obtained (a state where the MPR image is displayed), whereby the two-dimensional image corresponding to any one of the reference cross-sections can be obtained, and the basic function of the examination support function of the heart can be maintained.

According to the ultrasonic diagnostic equipment described above, in the heart examination, the ideal MPR position corresponding to the reference cross-section position of the heart is set to the volume data obtained by the three-dimensional ultrasound scanning, and in consequence, the ideal MPR image corresponding to the set MPR position can easily and rapidly be obtained. Furthermore, the ultrasound-scanned region is automatically switched from the three-dimensional region to the two-dimensional region in a state where the ideal MPR image is obtained by the three-dimensional ultrasound scanning (a state where the user keeps holding the position of the two-dimensional array probe), whereby the cross-section of the subject corresponding to the ideal MPR position (the cross-section of the subject closest to the MPR position or the cross-section of the subject at the substantially same position as the MPR position) can correctly be scanned in the two-dimensional manner.

Therefore, the MPR image derived from the volume data can be visually recognized, and hence, for example, the MPR image and the like of a heart long axis including the heart apex portion can be easily and stably depicted by a person who is not an expert. Further, in the two-dimensional region within the subject corresponding to the ideal MPR position, the ultrasonic image can be depicted with a high spatial resolution and a temporal resolution, and hence a measurement accuracy necessary for the diagnosis can be improved. As the result, the reference cross-section by the correct two-dimensional scanning necessary for the examination of the heart is easily imaged even by a person who is not an expert, which can enhance the accuracy of the diagnosis using the reference cross-section and reproducibility.

Second Embodiment

Next, an ultrasonic diagnostic equipment 1 according to the second embodiment will be described. The ultrasonic diagnostic equipment 1 according to the present embodiment realizes the substantially same examination support function of the heart as that of the first embodiment by setting, to volume data, an MPR position corresponding to a desired position of a reference cross-section of the heart while referring to a three-dimensional image obtained by three-dimensional ultrasound scanning, and then changing a two-dimensional array probe to an one-dimensional array probe to switch an ultrasound scan region from a three-dimensional region to a two-dimensional region.

Figure 5:
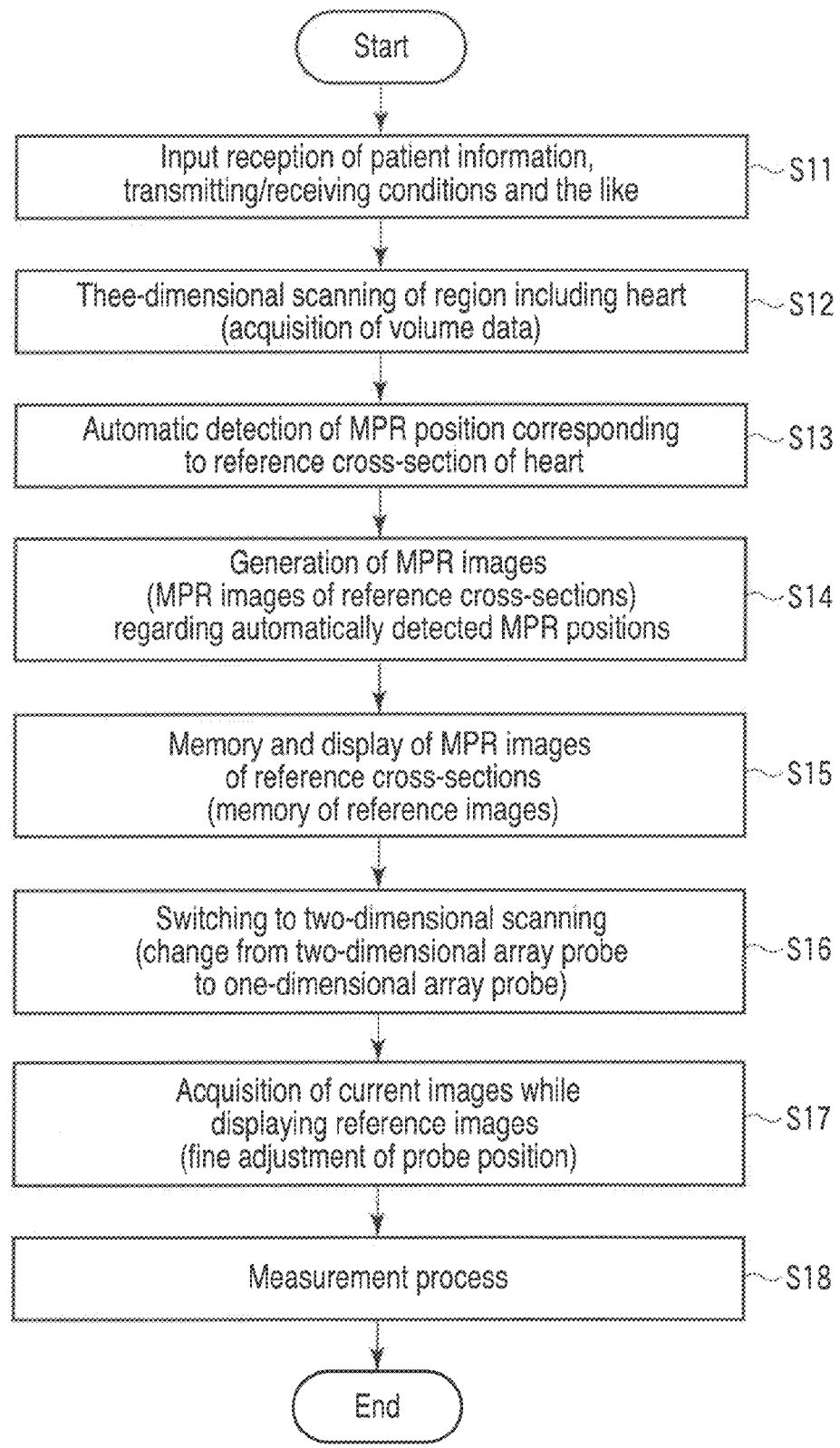
FIG. 5 is a flowchart showing a flow of a heart examination support process according to a second embodiment in accordance with a series of scan sequence.

FIG. 5 is a flowchart showing a flow of a heart examination support process according to the present embodiment in accordance with a series of scan sequence. Hereinafter, the contents of the respective steps of the flowchart in FIG. 5 will be described.

[Input Reception of Patient Information, Transmitting/Receiving Conditions and the Like: Step S11]

In the same manner as the first embodiment, patient information and transmitting/receiving conditions (an image angle, a focus position, a transmitting/receiving voltage and the like) and others are input through an operating unit 33. The thus input information and conditions are automatically stored in a memory device 22 (Step S11).

[Three-Dimensional Scanning of Region Including Heart: Step S12]

In the same manner as the first embodiment, a transmitting/receiving control unit 31 executes three-dimensional ultrasound scanning at a real time, with a region to be scanned being the three-dimensional region including the heart of a subject (Step S12).

[Automatic Detection of MPR Position Corresponding to Reference Cross-Section of Heart: Step S13]

In the same manner as the first embodiment, an image processing unit 19 automatically detects an MPR position corresponding to at least one of reference cross-sections of the heart with respect to at least one of the obtained volume data of the heart (Step S13).

[Generation, Display, and Memory of MPR Images Regarding MPR Positions: Steps S14 and S15]

In the same manner as the first embodiment, the image processing unit 19 generates an MPR image regarding the MPR position automatically detected on each volume data (Step S14). The generated MPR image is sequentially displayed on the display unit 23 at a real time. Further, in response to a predetermined operation (e.g., a freeze operation) from the operation unit 33, the displayed MPR image is displayed as a still image on the display unit 23, and is simultaneously and automatically stored in the memory device 22 as a reference image (Step S15).

[Switching to Two-Dimensional Scanning, and Acquisition of Two-Dimensional Images: Steps S16 and S17]

Then, a user changes an ultrasound probe from a two-dimensional array probe to one-dimensional array probe. The transmitting/receiving control unit 31 executes a predetermined operation from, for example, the operating unit 33. For example, in response to a switching button of the ultrasound probe, the transmitting/receiving control unit 31 scans a two-dimensional region (Step S16). After the switching, two-dimensional images (current images) regarding the cross-sections of a subject corresponding to the MPR positions are sequentially obtained. The obtained two-dimensional images are displayed on the display unit 23 at a real time simultaneously with the stored MPR images (reference images) in Step S15 (see FIG. 3). The user adjusts the holding position of the probe while referring to the displayed reference images, and when the two-dimensional images sufficiently close to (at the substantially same position as the position of) the reference images are obtained, a freeze button is pushed down. The image control unit 21 stores, in the memory device 22, the two-dimensional images at a time when the freeze button has been pushed down (Step S17).

[Measurement Process: Step S18]

In the same manner as the first embodiment, a measurement processing unit 25 executes a predetermined measurement process by use of the two-dimensional images regarding the correct reference cross-sections obtained in Step S17 (Step S18).

According to the ultrasonic diagnostic equipment described above, in the examination of the heart, the MPR position corresponding to the position of the reference cross-section of the heart is set to the volume data obtained by the three-dimensional ultrasound scanning, whereby the MPR image corresponding to an ideal MPR position can easily and rapidly be obtained. Further, the two-dimensional array probe is changed to one-dimensional array probe in a state where the ideal MPR image is displayed as the reference image by the above three-dimensional ultrasound scanning, whereby the ultrasound scan region is switched from the three-dimensional region to the two-dimensional region. After the switching, the two-dimensional image (the current image) and the reference image obtained at a real time through the one-dimensional probe are simultaneously displayed side by side. The user compares the reference image with the current image to finely adjusts the position and the direction of the one-directional array probe, whereby it is possible to obtain the current image which becomes the substantially same as the reference image. In consequence, the substantially same effect as the first embodiment can be realized.

In the present embodiment, owing to operation of switching the ultrasound probes, the easiness of depicting the same cross-section as the MPR image and the degree of the reproducibility are lower than in the case of the first embodiment. On the other hand, the two-dimensionally scanned image by the one-dimensional array probe generally has a higher image quality than the two-dimensionally scanned image by the two-dimensional array probe, and hence the present embodiment has an advantage that the two-dimensional image of a relatively higher image quality can finally be obtained.

It is noted that the above embodiments are not limited to the description given above, but the respective constitutional components can be modified and embodied in practical stages without departing from the gist thereof. Concrete modified examples are as follows.

(1) The respective functions in the above embodiments can be realized by installing programs for executing the processes in a computer such as a workstation and developing them on a memory. The above programs, which can cause the computer to execute the processes, can be stored in recording media such as magnetic disks (floppy (registered trade mark) disks, hard disks and others), optical disks (CD-ROMs, DVDs and others), and semiconductor memories, and can be distributed.

(2) In the above embodiments, the predetermined measurement processes have been executed by use of the two-dimensional images regarding the correct reference cross-sections. However, the embodiments are not limited, and the measurement processes may be executed by use of the MPR image in a desired time phase, if possible.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic equipment which separately executes two-dimensional ultrasound scanning and three-dimensional ultrasound scanning in a subject, comprising:
   a processor which detects a multiplanar reconstruction (MPR) position corresponding to at least one predetermined reference cross-section of a heart of the subject by use of at least one volume data obtained by executing the three-dimensional ultrasound scanning over a three-dimensional region containing at least a portion of the heart of the subject;
   an image generating unit which generates an MPR image corresponding to the detected MPR position from the at least one volume data;
   a display which displays the MPR image; and
   an image acquisition unit which automatically switches an ultrasound scanning region from the three-dimensional region to a two-dimensional region in the subject, the two-dimensional region being determined by the MPR position, and executes the two-dimensional ultrasound scanning over the two-dimensional region to obtain a two-dimensional image regarding the two-dimensional region.

2. The ultrasonic diagnostic equipment according to claim 1, wherein the image acquisition unit executes the two-dimensional ultrasound scanning over the two-dimensional region determined by the MPR position so that the two-dimensional image becomes substantially the same as the MPR image corresponding to the MPR position.

3. The ultrasonic diagnostic equipment according to claim 1, wherein the image acquisition unit executes the three-dimensional ultrasound scanning over the three-dimensional region followed by the two-dimensional ultrasound scanning over the two-dimensional region by use of a same ultrasound probe.

4. The ultrasonic diagnostic equipment according to claim 1, wherein the image acquisition unit executes the three-dimensional ultrasound scanning over the three-dimensional region and the two-dimensional ultrasound scanning over the two-dimensional region by use of different ultrasound probes.

5. The ultrasonic diagnostic equipment according to claim 1, wherein the processor further executes a measurement process of the heart by use of the two-dimensional image.

6. The ultrasonic diagnostic equipment according to claim 1, wherein the processor detects any one of a 4-chamber view, a 2-chamber view, an apical long axis view, and a short axis view of the left ventricle as the at least one predetermined reference cross-section of the heart.

7. The ultrasonic diagnostic equipment according to claim 1, wherein the display simultaneously displays at least the two-dimensional image and the MPR image.

8. An ultrasonic image processing apparatus, comprising:
   an image acquisition unit which automatically switches an ultrasound scanning region from a three-dimensional region to a two-dimensional region in the subject, the two-dimensional region being determined by a multiplanar reconstruction (MPR) position, and executes the two-dimensional ultrasound scanning over the two-dimensional region to obtain a two-dimensional image regarding the two-dimensional region, wherein the MPR position corresponds to at least one predetermined reference cross-section of the heart of the subject and is detected by use of at least one volume data, which is obtained by executing three-dimensional ultrasound scanning over the three-dimensional region containing at least a portion of the heart;
   a memory which stores the two-dimensional image and the at least one volume data;
   a display which displays at least the two-dimensional image; and
   a processor which executes a measurement process of the heart by use of the displayed two-dimensional image.

9. The ultrasonic image processing apparatus according to claim 8, wherein the two-dimensional image is obtained by two-dimensional ultrasound scanning over the two-dimensional region determined by the MPR position so that the two-dimensional image becomes substantially the same as an MPR image corresponding to the MPR position.

10. The ultrasonic image processing apparatus according to claim 8, wherein the two-dimensional image is obtained by the three-dimensional ultrasound scanning over the three-dimensional region followed by the two-dimensional ultrasound scanning over the two-dimensional region with the same ultrasound probe.

11. The ultrasonic image processing apparatus according to claim 8, wherein the two-dimensional image is obtained by the three-dimensional ultrasound scanning over the three-dimensional region and the two-dimensional ultrasound scanning over the two-dimensional region with different ultrasound probes.

12. The ultrasonic image processing apparatus according to claim 8, wherein the MPR position which becomes a reference is any one of a 4-chamber view, a 2-chamber view, an apical long axis view and a short axis tomography of the left ventricle as the at least one predetermined reference cross-section of the heart.

13. The ultrasonic image processing apparatus according to claim 8, wherein the display simultaneously displays at least the two-dimensional image and an MPR image.

* * * * *